United States Patent [19]

Ruesch

[11] Patent Number: 4,708,270

[45] Date of Patent: Nov. 24, 1987

[54] DRIPLESS SYRINGE

[75] Inventor: Merlin R. Ruesch, Chagrin Falls, Ohio

[73] Assignee: Loctite Corporation, Newington, Conn.

[21] Appl. No.: 866,986

[22] Filed: May 16, 1986

Related U.S. Application Data

[63] Continuation of Ser. No. 720,476, Apr. 8, 1985, abandoned, which is a continuation of Ser. No. 475,880, Mar. 16, 1983, abandoned.

[51] Int. Cl.$^4$ .............................................. B67D 5/42
[52] U.S. Cl. .................................. 222/386.5; 604/218
[58] Field of Search ..................... 222/386, 386.5, 327, 222/326; 604/218, 187

[56] References Cited

U.S. PATENT DOCUMENTS

| | | | |
|---|---|---|---|
| 2,833,451 | 5/1958 | Sherbondy | 222/327 |
| 2,923,442 | 2/1960 | Maras | 222/327 |
| 3,029,985 | 4/1962 | Krueger et al. | 222/386.5 |
| 3,193,146 | 7/1965 | Isgriggs et al. | 222/326 |
| 3,237,815 | 3/1966 | Ogle | 222/386 |
| 3,253,592 | 5/1966 | Pechmann | 222/386 |
| 3,315,847 | 4/1967 | Trumbull | 222/386.5 |

FOREIGN PATENT DOCUMENTS

| | | | |
|---|---|---|---|
| 1260103 | 5/1970 | Sweden | 604/218 |
| 878456 | 9/1961 | United Kingdom . | |
| 1000756 | 8/1965 | United Kingdom . | |
| 1133988 | 11/1968 | United Kingdom . | |
| 2020254 | 11/1979 | United Kingdom . | |

Primary Examiner—Joseph J. Rolla
Assistant Examiner—Kenneth Noland
Attorney, Agent, or Firm—Perman & Green

[57] ABSTRACT

A dripless syringe for dispensing a material such as glue, caulking, cement, foods, cosmetics, paint, oil, pharmaceuticals; etc., and any other materials suitable for dispensing thereby. The syringe plunger includes a generally hemispherically-shaped piston portion for pushing the material out of the syringe. Except for the piston portion, the plunger slides easily within a barrel of the syringe. In operation, the hemispherical piston portion is deformed during dispensing, but returns to its original shape after dispensing is finished. Upon returning to its original shape, the piston portion stops further dispensing of the material from the syringe.

1 Claim, 8 Drawing Figures

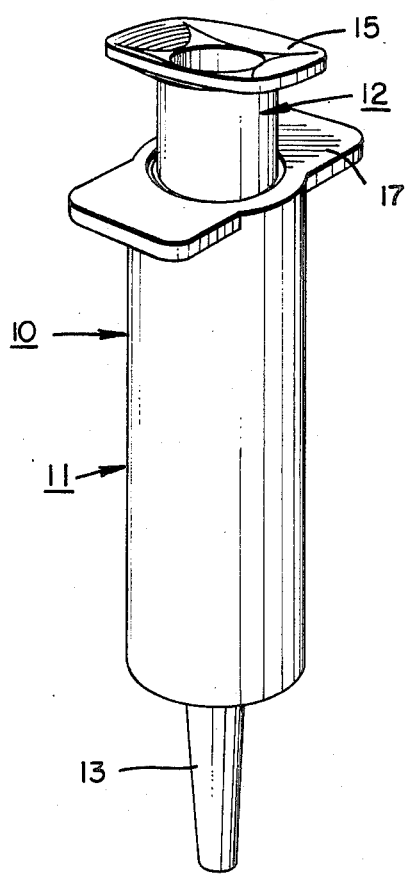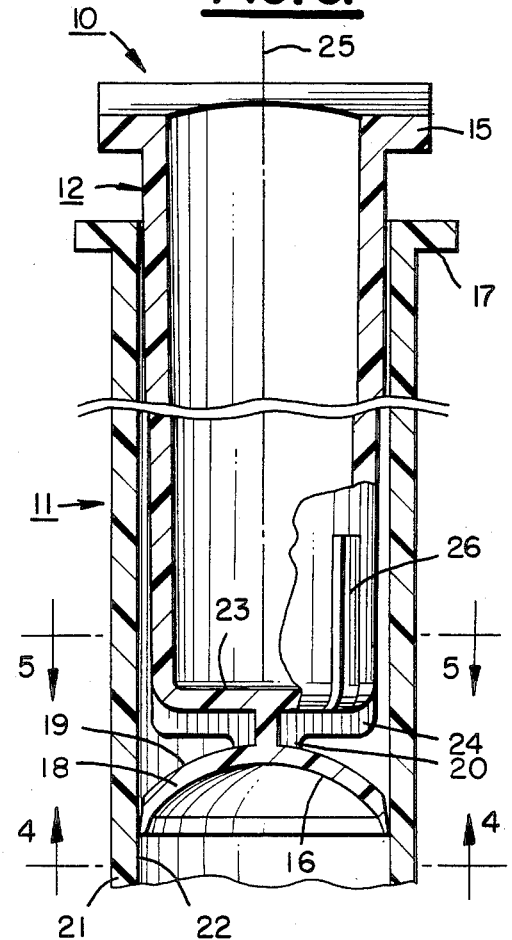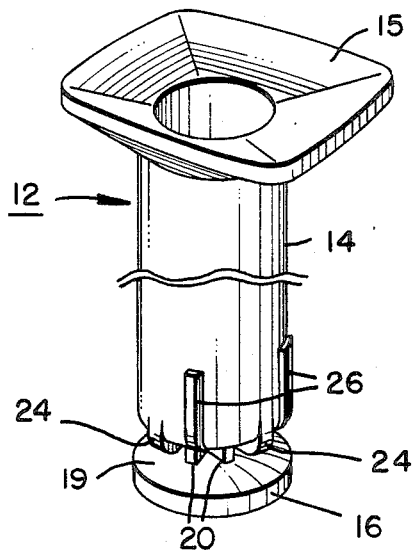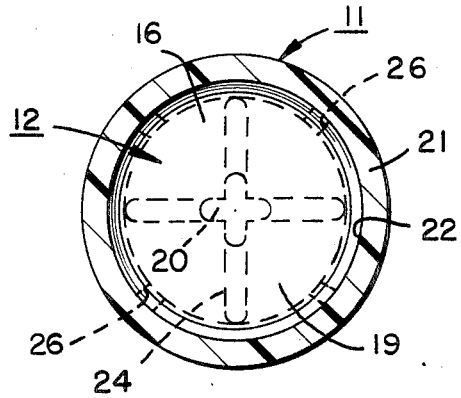

DRIPLESS SYRINGE

This is a continuation of co-pending application Ser. No. 720,476 filed on Apr. 8, 1985 now abandoned, which is a continuation of co-pending application Ser. No. 475,880 filed on Mar. 16, 1983 now abandoned.

BACKGROUND OF THE INVENTION

This invention relates to a no-drip syringe adapted for dispensing one or more materials. For example, the syringe can be used to dispense glue, caulking, cement, foods, cosmetics, paint, oil, pharmaceuticals; etc., and any other materials suitable for dispensing thereby comprising a single material or multiple materials as desired. In accordance with this invention, the direction in which the material being dispensed flows during the dispensing operation is reversed when the dispensing operation ends. This reversal of the direction of material flow stops the flow of material from the syringe when it is no longer desired to dispense material from the syringe.

In most prior art syringes, one has to pull back on the plunger in order to stop the flow of material out of the syringe spout. It is also known to utilize a spring which acts on the plunger to automatically pull it back when the pressure on the plunger is released. However, such an approach is unduly complicated and expensive.

Accordingly, the invention disclosed herein provides an infrared no-drip syringe. It has a configuration which can include a minimum of parts and is easy to operate.

SUMMARY OF THE INVENTION

In accordance with the present invention, a no-drip syringe is provided which overcomes the deficiencies in the prior art approaches. The syringe comprises a dispensing body for supporting at least one column of the material to be dispensed. At least one plunger comprising an elongate member is provided with an actuating pad at one end of the member and a piston portion at the opposing end thereof. The piston portion is adapted to act upon the at least one column of material to dispense it from the syringe dispensing body.

In accordance with this invention, a no-drip system is provided for substantially stopping the dispensing of the material being dispensed when the at least one plunger is not being actuated. The no-drip system comprises the piston portion itself which is configured to have a preferred generally hemispherical shape with a concave hollow face for acting on the material being dispensed. The piston portion is resilient. Means are provided for deforming the piston portion from the preferred shape during a dispensing operation while allowing the piston portion to return to its preferred shape after the dispensing operation is stopped.

The deforming means preferably comprises a portion of the plunger connecting the piston portion to the elongate member. Preferably, the syringe body includes at least one chamber for supporting therein at least one column of material. The chamber itself comprises a barrel portion having a longitudinally extending internal wall surrounding the material. Preferably, the elongate member is arranged to slide loosely within the barrel portion and the piston portion is arranged to move within the barrel portion with generally sealing engagement with the internal wall.

The elongated member, preferably, comprises a central longitudinally-extending core having a plurality of longitudinal flanges extending radially outwardly from the core with the radial extent of the flanges being selected so that the member is adapted to loosely slide within the barrel portion. The connecting portion, preferably, has a radial extent which is substantially smaller than the radial extent of the flanges. The piston portion, preferably, includes a convex face opposing the concave face and the connecting portion is, preferably, connected to a central portion of the convex face.

If desired, the syringe, in accordance with this invention, can include means resistant to chemical attack by the material being dispensed supported by the piston portion. One such means comprises a grommet supported by the piston portion which is adapted to cooperate with the hemispheric face of the piston portion so as not to interfere with the no-drip operation of the syringe. Preferably, the elongate member, the pad portion, the connecting portion and the piston portion comprise a unitary member which may be formed or molded of a material such as plastic.

BRIEF DESCRIPTION OF THE DRAWINGS

FIG. 1 is a perspective view of a no-drip syringe in accordance with the present invention.

FIG. 2 is a perspective view of a plunger in accordance with one embodiment of the invention for use in the syringe in FIG. 1.

FIG. 3 is partial cross-sectional view of the syringe in FIG. 1.

FIG. 4 is a cross-sectional view along the line 4—4 in FIG. 3.

DETAILED DESCRIPTION OF THE PREFERRED EMBODIMENTS

Figure 5:
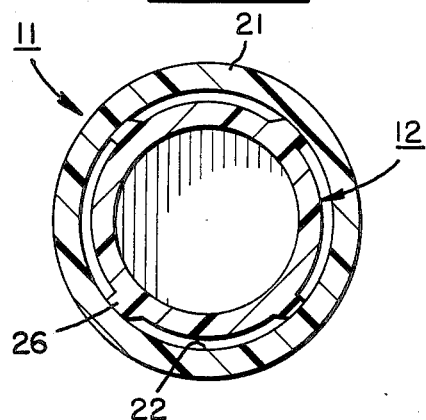
FIG. 5 is a cross-sectional view along the line 5—5 in FIG. 3.

Referring to FIG. 1, a no drip or dripless syringe is shown. The syringe 10 is comprised of a dispensing body 11 for supporting at least one column of the material to be dispensed. The syringe 10 also includes at least one plunger 12 for acting upon the column of material to be dispensed to dispense it from the syringe 10 via spout 13.

Referring now to FIG. 2, the plunger 12 is shown in greater detail. The plunger 12 comprises an elongated member 14 having an actuating pad portion 15 at one end and a piston portion 16 at the opposing end of the member 14. The piston portion 16 is adapted to act upon the column of material to be dispensed from the syringe 10 to push the material through the spout 13 as in FIG. 1 so that it can be applied by the operator as desired. The pad portion 15 is adapted to be engaged, for example, by the operator's thumb, in order to apply pressure to the plunger 12 so as to dispense the material from the syringe 10. Referring to FIG. 1, the dispensing body 11 includes a finger support flange 17 at its end opposing the spout 13. Therefore, in operation, a person supports the dispensing body 11 by two fingers disposed under the flange 17 on either side of the body 11 and presses with the thumb against the pad portion 15 of the plunger 12.

When pressure is thus applied to the pad portion 15, the material in the syringe is dispensed therefrom by flowing in a first direction out of the spout 13. In accordance with this invention, a no-drip system is provided for substantially stopping the dispensing of the material when the pressure is removed from the plunger so that it is not being actuated to dispense the material.

Referring now to FIGS. 2-5, the no-drip system to provide the no-drip operation is described in greater detail. The piston portion 16 is configured to have a preferred generally hemispherical shape with a concave hollow face 18 for acting on the material being dispensed. The piston portion 16 is resilient so that if it is deformed it springs back to its preferred generally hemispherical shape. The term "hemispheric shape" as used herein is not intended to be limited to a full hemisphere since it can comprise a portion of the hemisphere as shown. Further, it does not have to be exactly hemispheric, but rather it should have a generally arcuate shape as shown comprising a hollow face 18 facing the material being dispensed and a convex opposing face 19 which is, preferably, of a correspondingly arcuate nature.

The piston portion 16 having the generally hemispheric shape acts in a manner analagous to the bottom of an oil can. When not in use, the plunger 12 and the hemispheric concave face 18 sit on top of a column of the material to be dispensed. At this point, the hemispheric face 18 has its desired preferred profile. When pressure is applied to the thumb pad 15, the hemispheric face 18 is generally flattened out by the action of the central connecting portion 20. This action changes the shape of the hemispherical face 18 from its natural preferred shape, as shown in FIG. 3, into a more flattened out shape. The more flattened out shape generally has an effective radius of larger dimension than the radius of the face 18 in its preferred preformed profile. As the face 18 is flattened out, the column of material being dispensed (not shown) is pushed downwards through the spout 13 as in FIG. 1.

When the proper amount of material has been dispensed, the operator removes his thumb from the pad 15 thereby releasing the pressure on the plunger 12. The piston portion 16 is formed of a resilient material having sufficient springiness so that when the pressure on the plunger is released, the piston portion tends to return to its preferred shape. This automatically pushes the plunger 12 upwardly away from the material being dispensed. The tendency of the hemispherical piston portion 16 to return to its preferred shape causes the shape of any void between the concave face 18 and the top of the column of the material being dispensed to change. This, in turn, causes a reduced pressure which further causes the material being dispensed to be drawn up into the barrel 21 of the syringe 10 from the spout 13 thereby immediately stopping the flow of the material and holding it there until pressure is again applied to the plunger 12.

The elongated member portion 14 of the plunger 12 is arranged to slide easily within the barrel 21 of the dispensing body 11. In contrast, the piston portion 16 is arranged to move within the barrel portion 21 in a generally sealing engagement with the internal wall 22 of the barrel portion.

Figure 6:
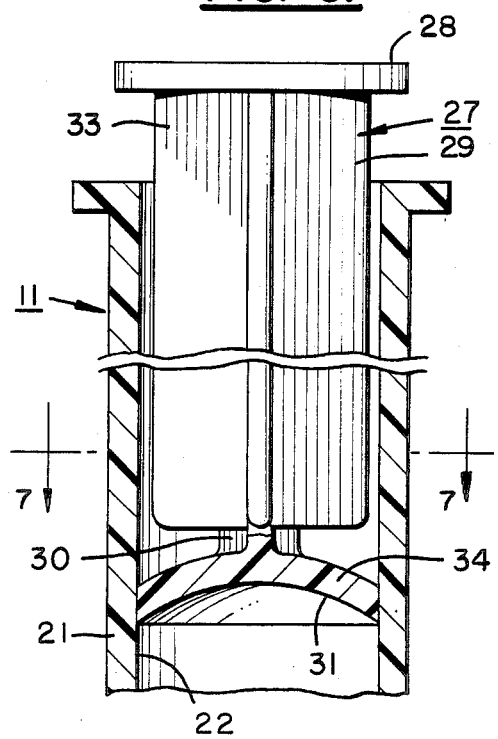
FIG. 6 is a partial cross-sectional view of a dripless syringe in accordance with another embodiment of this invention.

The plunger 12 can comprise a hollow member as in the embodiment of FIG. 3 or a solid member as in the embodiment of FIG. 6. Referring to FIGS. 3-5, the plunger 12 elongated member 14 comprises a cylindrical body extending from the actuating pad portion 15 at one end and has a bottom portion 23 closing off the opposing end of the elongated member 14. The piston portion 16 is connected to the bottom portion 23 of the elongated member 14 by connecting portion 20.

The connecting portion 20 includes radially extending support ribs 24. The support ribs 24 extend radially outwardly from a central axis 25 of the plunger 12 to a greater extent for the section adjacent the bottom portion 23 and to a much lesser extent for the section adjacent the piston portion 16. This is important since the portion of the connecting portion 20 adjacent the piston portion 16 acts as a means for deforming the piston portion from its preferred generally hemispherical shape to flatten it out during a dispensing operation. It also allows it to return to its preferred shape after the dispensing operation is over.

In order to guide plunger 12 within the barrel 21, a plurality of flanges 26 are arranged about the barrel 21 so as to extend radially outwardly therefrom. The radial extent of the flanges 26 is selected so as to just engage the internal wall 22 of the barrel 21 to permit easy sliding of the plunger 12 within the dispensing body 11. The longitudinal extent of the flanges 26 is limited to only a small portion of the elongated member 14 adjacent the end thereof to which the piston portion 16 is attached. The flanges 26 are so limited in order to permit the plunger 12 to slide easily within the barrel 21.

Preferably, the plunger 12 as shown comprises a unitary body including the elongated member 14, the actuating pad portion 15, the piston portion 16 and the connecting portion 20. The plunger 12 may be formed of any desired material, but, preferably, is molded of an inexpensive material such as plastic.

Since only the piston portion 16 has a substantial frictional engagement with the internal wall 22 of the barrel 21, the piston portion 16 can easily return to its preferred shape after a dispensing operation by moving the plunger 12 in a direction away from the material being dispensed.

Figure 7:
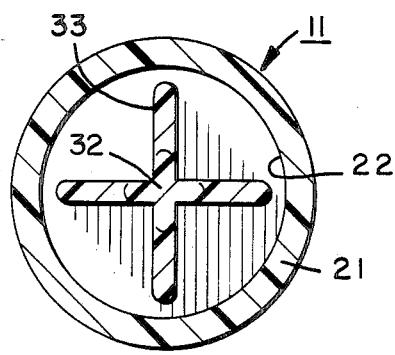
FIG. 7 is a cross-sectional view along the line 7—7 in FIG. 6.

Referring now to FIGS. 6 and 7, a particularly preferred plunger design is shown. The plunger 27 shown in FIGS. 6 and 7 also, preferably, comprises a unitary body, including an actuating pad portion 28, an elongated member 29, a connecting portion 30 and a piston portion 31. The piston portion 31 is essentially the same as described in reference to the embodiment of FIGS. 2-5.

The plunger 27 differs from the plunger 12 principally in the use of a solid elongated member 29. The elongated member 29 comprises a central longitudinally extending core 32 having a plurality of longitudinally extending flanges 33 extending radially outwardly from the core 32. The radial extent of the flanges can be selected so that the elongated member is adapted to loosely sit within the barrel 21. The connecting portion 30 comprises a portion of a flange 33 wherein the radial extent of the flange 33 has been substantially reduced as compared to the remainder of the elongate body 29. As in the previous embodiment, it is important that the radial extent of the connecting portions 30 be relatively small and that the portion 30 be centrally located so as to act on the generally hemispherically-shaped piston portion 31 to flatten it out during a dispensing operation. The connecting portion 30 is connected to a central portion of the convex face 34 of the piston portion 31.

Referring now to FIGS. 1, 3, and 6, it should be apparent that the dispensing body 11, and barrel 21 in combination with the spout 13 define a chamber for supporting the at least one column of the material to be dispensed. The syringes have been illustrated thus far, as including a single barrel 20. If desired, they could include plural barrels and a corresponding plurality of plunges 12 or 27. Further, if desired and in accordance with known prior art techniques, the plungers 12 can be joined together so that they are actuated in common. In such a plural barrel syringe arrangement, there can be separate multiple chambers for supporting separate and, if desired, distinct materials to be dispensed. A syringe can employ common spout 13 communicating with each of the chambers or it can comprise a separate spout for each chamber.

Figure 8:
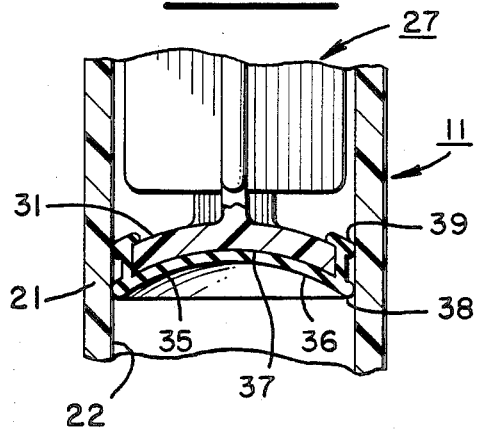
FIG. 8 is a partial cross-sectional view of a dripless syringe in accordance with yet another embodiment of this invention.

On occasion, the material selected to form the plunger 12 or 27 may react chemically with the material being dispensed. In prior art approaches, this problem has been overcome by the use of a grommet which is chemically resistant to the material being dispensed. The grommet is supported by the plunger 12, if desired. In accordance with this invention, a grommet 35 as shown in FIG. 8 can be similarly employed. In this embodiment, the radial extent of the piston portion 31 has been reduced to allow the grommet to be flipped over the piston portion. The grommet 35 shown has a concave portion 36 generally conforming to the concave face 37 of the piston portions 31.

It is not necessary for the grommet 35 to be springy or resilient as in the case of the previously described piston portions 31. However, it can be formed of a relatively flexible material so that it conforms to the shape of the concave face 37 in operation. The edge portions 30 of the grommet include a plurality of ridges 39 for sealingly engaging the internal wall 22 of the barrel 21. In operation, the concave portion 36 of the grommet 35 conforms to the shape of the piston portion 31. Therefore, the operation of the plunger 12 or 27 including a grommet 35 is essentially the same as previously described in reference to FIGS. 2–7. Accordingly, the grommet 35 acts to insulate the material being dispensed from the piston portion 31 while not interfering with the intended action of the hemispherically shaped piston portion.

The syringe, in accordance with this invention, can be used to dispense thin as well as thick materials; namely, materials having any desired viscosity. It can be used to dispense any suitable material and is not limited in application to the materials specifically mentioned herein.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. In a no-drip syringe for dispensing a material comprising:
   (a) a dispensing body for supporting at least one column of said material; and
   (b) at least one plunger, said plunger comprising an elongate member, an actuating pad portion at one end of said member, and a piston portion at an opposing end of said member for acting upon said at least one column of said material to dispense it from said dispensing body, said dispensing body including at least one chamber supporting said at least one column of said material, said chamber comprising a barrel portion having a longitudinally extending internal wall surrounding said material and, wherein said member is arranged to slide loosely within said barrel portion and said piston portion is arranged to move within said barrel in generally sealing engagement with said internal wall, said member comprising a central longitudinally extending core having a plurality of longitudinal flanges extending radially outwardly from said core with the radial extent of said flanges being selected so that said member is adapted to loosely slide within said barrel portion;
   (c) no-drip means for substantially stopping the dispensing of said material when said at least one plunger is not being actuated to dispense said material; said no-drip means comprising:
   (d) said piston portion having a preferred generally hemispherical shape with a concave hollow unobstructed face for acting on said material, said piston portion being resilient and including a convex face opposing said concave face and wherein said connecting portion is connected to a central portion of said convex face;
   (e) means for deforming said piston portion from said preferred shape during a dispensing operation and for allowing said piston portion to return to its preferred shape after said dispensing operation is stopped, said deforming means comprising a centrally located portion of said plunger connecting said piston portion to said member, said connecting portion having a radial extent which is substantially smaller than the radial extent of said flanges;
   (f) said elongate member, said pad portion, said connecting portion, and said piston portion comprising a unitary member and
   (g) means resistant to chemical attack by said material supported by said piston portion, said last mentioned means comprising a grommet supported by said piston portion, said grommet cooperating with said hemispheric face of said piston portion so as not to interfere with the no-drip operation of said syringe, said grommet having a concave portion generally conforming to the concave face of said piston portion.

* * * * *